United States Patent [19]

Cohen

[11] Patent Number: 4,521,185
[45] Date of Patent: Jun. 4, 1985

[54] HIGH VOLUME ORAL EVACUATOR

[76] Inventor: Alan P. Cohen, 50 Mill Rd., Eastchester, N.Y. 10709

[21] Appl. No.: 525,446

[22] Filed: Aug. 22, 1983

[51] Int. Cl.³ .......................... A61C 1/00; A61C 3/00
[52] U.S. Cl. .......................................... 433/31; 433/93
[58] Field of Search .............................. 433/31, 93, 91

[56] References Cited

U.S. PATENT DOCUMENTS 2,176,620 10/1939 Beam ...................................... 433/31
3,299,511 1/1967 Hutson .................................. 433/96
3,777,756 12/1973 Lohr ...................................... 433/31

FOREIGN PATENT DOCUMENTS 446545 3/1949 Italy ...................................... 433/31

Primary Examiner—John J. Wilson
Attorney, Agent, or Firm—Richard L. Miller

[57] ABSTRACT

A high volume oral evacuator is provided and consists of a modified dental aspirator with an adjustable mirror placed at the end of the tool that is capable of performing all the reflective and retractive procedures in a patient's mouth.

1 Claim, 8 Drawing Figures

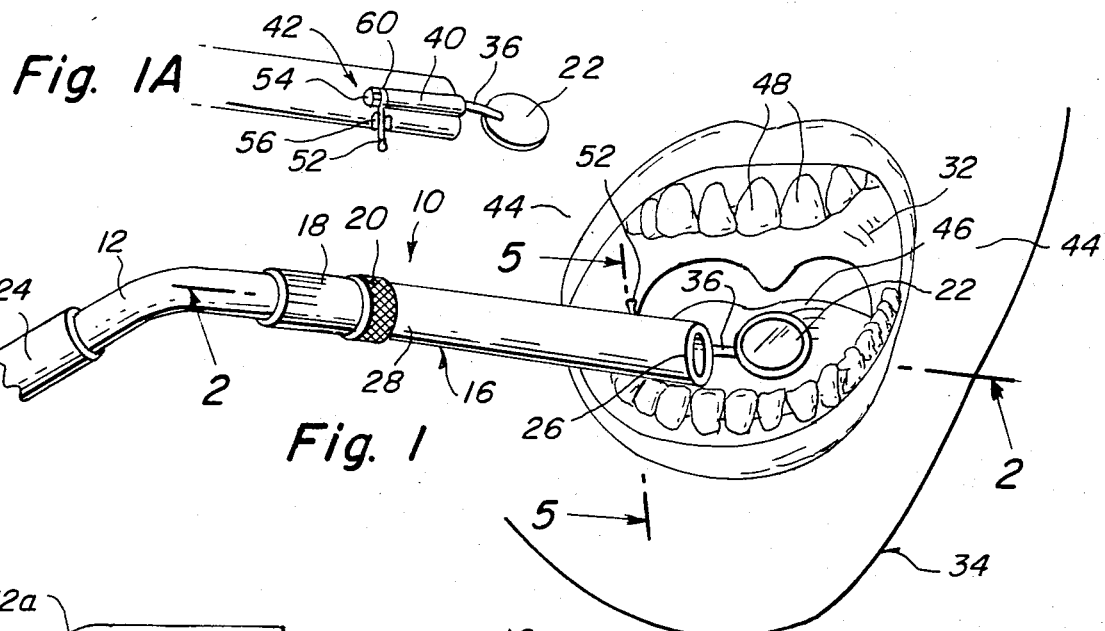
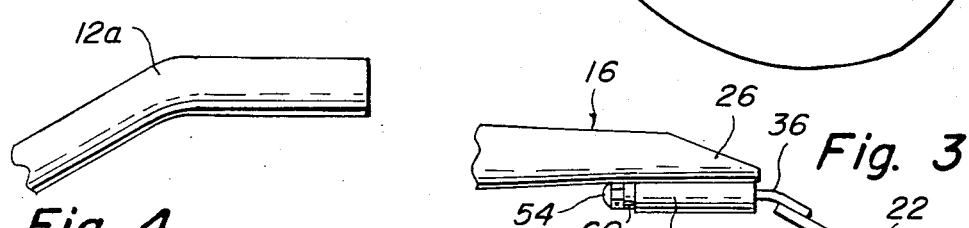
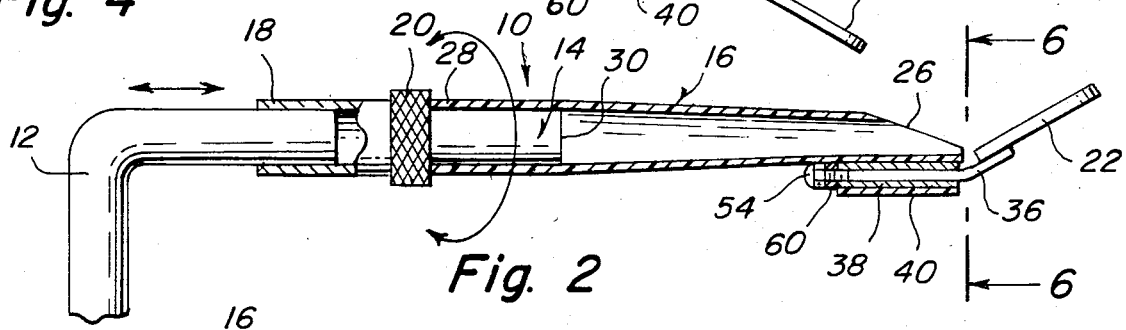
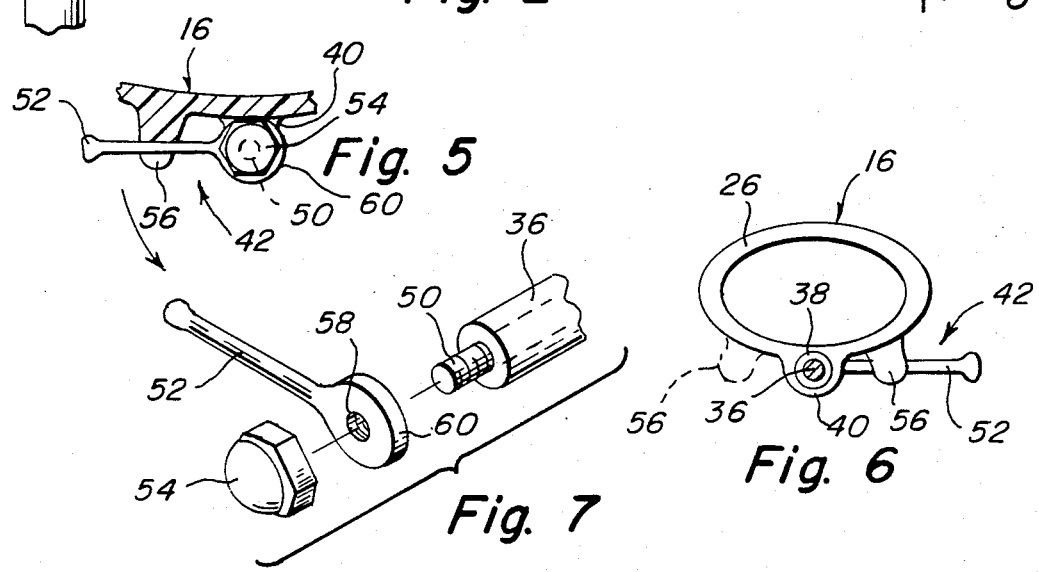

HIGH VOLUME ORAL EVACUATOR

BACKGROUND OF THE INVENTION

The instant invention relates generally to dental tools and more specifically it relates to a high volume oral evacuator.

The standard way for a right handed dentist to work is to hold a high speed drill in his right hand and a mirror in his left hand. The mirror acts not only as a tool to operate indirectly through reflection in the upper mouth, but also as a retractor for the cheek and tongue in the lower mouth. It can also reflect light onto the teeth. In the standard method it is desirable to have high volume oral evacuation performed in order to remove the large amounts of water sprayed out of the high speed drill. The evacuation must be performed by a third hand, such as an assistant to the dentist.

It is understood that numerous dental tools have been provided in prior art that are adapted to be used in a patient's mouth for various similar purposes. For example, U.S. Pat. Nos. 2,779,100; 2,823,455; 2,862,299 and 3,299,511 all are illustrative of such prior art. While these units may be suitable for the particular purpose to which they address, they would not be as suitable for the purposes of the present invention as heretofore described.

SUMMARY OF THE INVENTION

A principle object of the present invention is to provide a high volume oral evacuator that combines an intra-oral high volume evacuator tip and a mirror in one instrument.

Another object is to provide a high volume oral evacuator that has a mirror capable of performing all the reflective and retractive procedures.

An additional object is to provide a high volume oral evacuator that may be better placed at the site of operation.

A further object is to provide a high volume oral evacuator that is simple and easy to use.

A still further object is to provide a high volume oral evacuator that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is the perspective view of the invention positioned within the mouth of a patient.

FIG. 1A is a partial bottom perspective view of the invention.

FIG. 2 is an enlarged cross sectional view taken along line 2—2 of FIG. 1 showing a right angle section attached thereto.

FIG. 3 is a partial view of the invention showing the mirror rotated down toward the tongue so the device may be used as a retractor.

FIG. 4 is a view of an alternate angle section that may be used with the invention.

FIG. 5 is an enlarged fragmentary cross sectional view taken on line 5—5 of FIG. 1 showing the arm holding ear portion and an arm in a locked position.

FIG. 6 is an enlarged cross sectional view taken on line 6—6 in FIG. 2 showing the bevelled intake end of the sleeve member.

FIG. 7 is an enlarged exploded view showing some construction details of the invention.

DESCRIPTION OF THE PREFERRED EMBODIMENT

Turning now descriptively to the drawings, in which similar reference characters denote similar elements throughout the several views FIGS. 1 through 7 illustrates a high volume oral evacuator that generally comprises a tubular handle 12, a tubular tip member 14, a rigid sleeve member 16, a friction joint flange 18, an operating ring 20 and a mirror 22.

The tubular handle 12 is adapted to be connected to a source of vacuum such as a flexible tube 24. The rigid sleeve member 16 has a bevelled intake end 26 with other end 28 secured over the tip member 14 and extending outwardly beyond outer end 30 of the tip member 14. A swivel joint is provided within operating ring 20 between the tip member 14 and the flange 18 whereby the tip member 14 may be freely rotated relative to the handle angle section 12 to variously position the bevelled intake end 26 of the sleeve member 16 within a mouth 32 of a patient 34.

The operating ring 20 is fixed to the tip member 14 adjacent the friction joint 18 in position to be manipulated for turning the tip member 14 relative to the handle angle section 12 by fingers of a hand of an operator (not shown) holding the handle angle section 12. The handle 12 angle section is of a ninety degree angle as best shown in FIG. 2. Other handle angle sections such as handle angle section 12a shown in FIG. 4 can be of a different angle.

The mirror 22 is connected to the bevelled intake end 26 of the rigid sleeve member 16 at an angle of about thirty degrees thereto. The mirror 22 has a shaft 36 pivotally supported on the rigid sleeve member 16 by a small tube 38 embedded into a small sleeve 40 formed integrally with rigid sleeve member 16, and adjacent to the bevelled intake end 26 thereof.

The high volume oral evacuator 10 further contains a device 42 for flipping over the mirror 22 and locking the shaft 36 in a stationary position. In the mirror facing an up position as best seen in FIGS. 1 and 2 the mirror 22 can be used as a viewing tool for the upper teeth 48.

The device 42 as best seen in FIGS. 5, 6 and 7 generally comprises a reduced threaded shaft member 50, an arm 52, a cap nut 54 and an arm holding ear portion 56.

The reduced threaded shaft member 50 is affixed to end of the shaft 36 of the mirror 22. The arm 52 has a transverse threaded aperture 58 in an enlarged end 60 thereof that is threadably mounted onto the reduced threaded shaft member 50 so that the arm 52 can flip over the mirror 22 via the shaft 36 of the mirror.

The cap nut 54 threadably mounts onto the reduced threaded shaft member 50 to secure the arm 52 thereon. The arm holding ear portion 56 is affixed to the rigid sleeve member 16 of either side of the shaft 36 of the mirror 22 for the right handed or left handed dentists. The arm 52 can engage the arm holding ear portion 56 thus preventing the arm 52 from moving therefrom.

When the mirror 22 and evacuator rigid sleeve member 16 are embodied in the same tool one task of an assistant is eliminated. The mirror 22 is capable of performing all the reflective and retractive procedures. The evacuator becomes better placed at the site of operation, by not competing for the same space as the mirror. The ability to flip the mirror 22 and swivel the rigid sleeve member 16 gives the mirror 22 flexibility in all modes.

The mirror 22 may also be detached and changed when it gets scratched or separately sterilized if desired. The device 42 permits the dentist to keep the mirror 22 stationary throughout its function yet it can be flipped with the same hand it is held with when desired.

In FIG. 6 it is to be noted that two ears are shown one in dotted lines this because it may be desirable to manufacture the device in such a manner that the user (dentist) can elect to cut one ear depending whether he is left handed or right handed etcetera. In any case the main purpose is to free the dentist from the need for an assistant during procedures that require water.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A high volume oral evacuator which comprises:
   (a) a tubular handle adapted to be connected to a source of vacuum;
   (b) a tubular tip member;
   (c) a rigid sleeve member having a bevelled tapered intake end with other end secured over said tip member and extending outwardly beyond outer end of said tip member;
   (d) means providing a swivel joint of said tip member with said handle whereby said tip member may be freely rotated relative to said handle to variously position the bevelled intake end of said sleeve member within a mouth of a patient;
   (e) an operating ring fixed to said tip member containing said swivel joint in position to be manipulated for turning said tip member relative to said handle by fingers of a hand of an operator holding said handle; and
   (f) a mirror connected at an angle to the bevelled tapered intake end of said sleeve member, wherein said mirror further comprises a shaft pivotally supported on said sleeve member and adjacent to the bevelled intake end thereof, that further comprises a means for flipping over said mirror and locking said shaft in a stationary position so that in a down position said mirror can be used as a retractor for cheeks and tongue and in a up position as a viewing tool for the upper teeth, wherein said means for flipping over said mirror and locking said shaft in a stationary position comprises;
   (i) a reduced threaded shaft member affixed to end of said shaft of said mirror;
   (ii) a arm having a transverse threaded aperture in enlarged end thereof that is threadably mounted onto said reduced threaded shaft member so that said arm can flip over said mirror via said shaft of said mirror;
   (iii) a nut threadably mounted onto said reduced threaded shaft member to secure said arm thereon; and
   (iv) at least one arm holding ear portion affixed to said rigid sleeve member on either side of said shaft of said mirror so that said arm holding ear portion thus prevents said arm from moving therefrom.

* * * * *